United States Patent [19]
Figura et al.

[11] Patent Number: 5,900,372
[45] Date of Patent: May 4, 1999

[54] **METHOD FOR THE CULTURE OF MICROORGANISMS OF THE *GENERA HELICOBACTER*, CAMPYLOBACTER AND ARCOBACTER EMPLOYING CULTURE MEDIA COMPRISING CYCODEXTRIN**

[75] Inventors: Natale Figura; Massimo Bugnoli, both of Monteriggioni; Roberto Olivieri, Constalpino; Rino Rappuoli, Monteriggioni, all of Italy

[73] Assignee: Chiron S.p.A., Italy

[21] Appl. No.: 08/295,081

[22] Filed: Aug. 24, 1994

Related U.S. Application Data

[63] Continuation of application No. 07/962,357, Oct. 16, 1992, abandoned.

[30] Foreign Application Priority Data

Oct. 31, 1991 [IT] Italy .................................. MI912904 U

[51] Int. Cl.$^6$ .............................. C12N 1/20; C08B 37/16
[52] U.S. Cl. .................................... 435/252.6; 435/253.6; 536/103; 536/124
[58] Field of Search .............................. 435/252.1, 253.6; 536/103, 124

[56] References Cited

U.S. PATENT DOCUMENTS 4,500,639  2/1985  Suzuki et al. .
4,687,738  8/1987  Ginnaga et al. .
4,965,205  10/1990 Quentin-Millet et al. ........... 435/252.1

OTHER PUBLICATIONS

G. E. Buck, et al., "Medium Supplementation for Growth of Campylobacter Pyloridis" *Journal of Clinical Microbiology* (1984) pp. 597–599.
Morrison et al, *Organic Chemistry* 4th Ed., p. 1111, 1983.
Buck and Smith Journal of Microbio 25(4) 1987 pp. 597–599 Medium Supplementation for Growth of Campylobacter.

*Primary Examiner*—Francisco C. Prats
*Attorney, Agent, or Firm*—Woodcock, Washburn, Kurtz, Mackiewicz & Norris; Alisa A. Harbin; Robert P. Blackburn

[57] ABSTRACT

Method for the culture of microorganisms of the genera Helicobacter, Campylobacter and Arcobacter, wherein culture media are employed, which comprise, in place of blood or its derivative, cyclodextrins, methylcellulose or mixtures thereof.

2 Claims, 2 Drawing Sheets

METHOD FOR THE CULTURE OF MICROORGANISMS OF THE *GENERA HELICOBACTER*, CAMPYLOBACTER AND ARCOBACTER EMPLOYING CULTURE MEDIA COMPRISING CYCODEXTRIN

This application is a continuation of application Ser. No. 07/962,357 filed Oct. 16, 1992, now abandoned.

TECHNICAL FIELD OF THE INVENTION

The present invention relates to a method for the culture of microorganisms of the genera Helicobacter, Campylobacter and Arcobacter, wherein culture media are employed, which comprise, cyclodextrins, methylcellulose or mixtures thereof.

BACKGROUND OF THE INVENTION

The culture on industrial scale of microorganisms of the genera Helicobacter, Campylobacter and Arcobacter is getting more and more important both for the production of relevant amounts of the same microorganisms and because of the importance of the products which can be produced during the fermentation culture or still for the manufacture of cheap media suitable for the primary isolation of microorganisms belonging to the aforementioned genera. With regard to the importance attained by the above cited microorganisms, it should be considered for instance that the *Helicobacter pylori* is recognized as the aetiological agent of type B gastritis, likely the second most disseminated chronic infection in the world after dental caries, and as co-agent of peptic ulcer. It is therefore evident that a more developed knowledge of the physiological and pathological properties of said microorganism, knowledge that at present is still very poor due to the difficulty involved in the cultivation, should be of extreme importance. The cultures of *H. pylori* are usually carried out by adding to the culture media blood or derivative thereof (serum, red cells etc.), yolk in concentration ranging between 5% and 20%. Said additives, obviously, cannot be employed on industrial scale because of the drawbacks deriving therefrom for the purification of the culture products, drawbacks which moreover involve high costs for the industry. It is therefore extremely interesting to avail a culture media wherein blood and derivatives thereof are replaced, entirely or partially, by products which do not bring about the above cited disadvantages, without compromising the culture yield though.

SUMMARY OF THE INVENTION

The present invention relates to methods for culturing microorganisms of the genera Helicobacter, Campylobacter, and Arcobacter, wherein the culture media employs cyclodextrins, methylcellulose, or mixtures thereof. Preferably, the cyclodextrin is selected from the group consisting of α-cyclodextrin, β-cyclodextrin, and γ-cyclodextrin; more preferably, methylated forms thereof. A preferred microorganism is *H. pylori*.

DETAILED DESCRIPTION OF THE INVENTION

Figure 1:
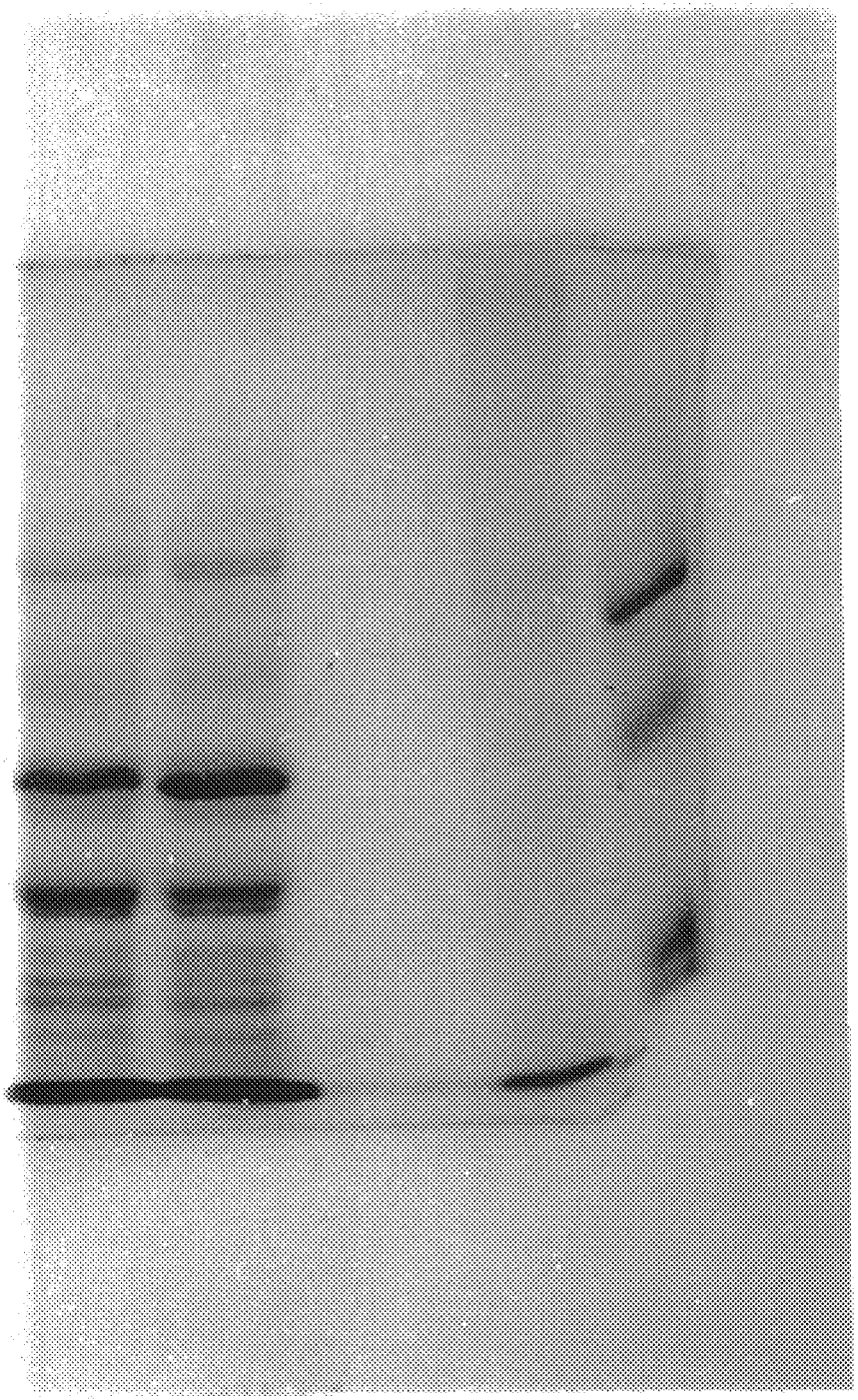
FIG. 1 compares the *H. pylori* cellular layer (130 kD protein) obtained in Example 1 with the cellular layer obtained via the traditional media.

It has been surprisingly discovered, and it makes the object of the present invention, that culture media wherein blood and its derivatives are, at least partially, replaced by cyclodextrins, methylcellulose or mixtures thereof, enable the microorganisms of the genera Helicobacter, Campylobacter and Arcobacter to be cultivated in the similar way and with yield even improved over those obtained with the traditional media.

The present invention therefore relates to a method for the culture of microorgansisms of the genera Helicobacter, Campylobacter and Arcobacter with the object of preparing the cell layer of the same microorganisms and/or the specific proteins of pharmaceutical interest produced by the same or still for manufacturing cheap culture media suitable for the primary isolation of microorganisms belonging to the aforementioned genera.

According to a specific embodiment of the present invention said culture method relates to the culture of *Campylobacter jejuni, Campylobacter coli, Campylobacter laridis, Campylobacter jejuni subsp. doylei*, "*Campylobacter upsaliensis*", *Campylobacter hyointestinalis*, "*Campylobacter fetus* subsp. *fetus*", "*Campylobacter fetus* subsp. *venerealis*", "*Arcobacter nitrofigilis*", "*Arcobacter cryaerophilus*". More specifically the invention relates to a method for the culture of *Helicobacter pylori*, and to the production of the about 130 kD protein associated to the cytotoxic and vacuolating activity as well as the protein exhibiting ureasic activity synthesised by the same microorganism.

According to a still more specific embodiment of the present invention, blood and/or derivatives thereof are entirely absent from the culture media. The culture is carried out on media, either solid or liquid, comprising cyclodextrins, methylcellulose or mixtures thereof.

In particular cyclodextrins selected from the group consisting of α-cyclodextrin, β-cyclodextrin and gamma-cyclodextrin, optionally methylated, are employed.

According to a specific embodiment of the invention dimethyl-O-βcyclodextrin is used.

The culture temperature may vary from 30° to 42° C., preferably is maintained at 37° C. The culture media is maintained under stirring and in microaerophylic conditions in presence of $CO_2$ and optionally $H_2$.

The 130 kD cytotoxin may be extracted from the biomass collected upon centrifugation of the culture media according to the procedure disclosed hereinafter.

After washing with phosphate buffer pH 7.4 (PBS) the cell layer is treated with a 6M guanidine HCl in PBS solution at room temperature under stirring. After centrifugation the supernatant is dialysed versus PBS and represents a fraction enriched in 130 kD cytotoxin. Urease may be purified from the same biomass according to the procedure reported hereinafter.

The pellet of bacterial cells is resuspended in 0.25M glycine HCl, pH3, 5 mM EDTA and incubated at 37° C. for 16 hours. The supernatant obtained upon centrifugation at 12,000 rpm, at 5° C. for 30 minutes in a centrifuge Beckman fitted with a JA 20 rotor is added with two volumes absolute acetone and cooled at −20° C. After keeping for 5 hours at said temperature, the proteic pellet is collected by centrifugation as already described and finally resuspended and dialysed in PBS.

The method according to the invention has not only simplified, as already said, the culture of the aforementioned microorganisms at issue and the recovery of the proteins produced by them, but it has also allowed the study of the biochemical and physiological (motility) features as well as the chemosensitivity and the pathogenicity of the *H. pylori* to be improved by simplifying it.

EXAMPLE 1

The strain of *H. pylori* is cultured on Petri dishes containing 20 ml of the agarized culture media Columbia Difco, modified with the addition of 1 g/l dimethyl-O-β-cyclodextrin.

The dishes, once inoculated, are incubated in microaerophylic atmosphere at high humidity level (about 95%) at temperature of 37° C. for 72–96 hours. When the cell layer is clearly apparent on the dishes, the method is prosecuted with the suspension, by means of a wad of sterile cotton wool, of the bacteria in Brucella media until an optical density equivalent to 9 McFarland is achieved. Five millilitres of this suspension are inoculated in a 2000 ml conical flask containing 500 ml Brucella Difco media modified by adding 1 g/l dimethyl-O-β-cyclodextrin, 2.5 mg/l $FeCl_2$, 2.5 mg/l amphotericin B, 10 mg/l trimethoprin, 5 mg/l vancomycin and 5 U/ml polymixin B. Other 5 millilitres are inoculated in a conic flask of the same size as the previous and containing the same medium, where however cyclodextrin is replaced by 50 g/l fetal serum. The conic flasks are incubated for 72 hours in a rotating incubator at 200 rpm at temperature 37° C. in microaerophylic atmosphere having the following composition: $N_2$ 75%, $CO_2$ 10%, $H_2$ 10% and $O_2$ 5%.

After said period the optic density is monitored at 590 nm and a subculture on Columbia agar/blood and a Gram staining are performed in order to verify the purity of the same culture.

The optic density obtained is equivalent to 7.8 in the conic flask with cyclodextrin and 4.8 in that with fetal serum. The amount of wet cellular layer recovered after centrifugation is equivalent to 8 g from the conic flask with cyclodextrin and 5 g from that with fetal serum.

Two samples, 5 g layer each, collected from cultures carried out, as reported above, with either cyclodextrin (CD) or fetal serum (FS) respectively, have been treated as follows: after washing with 100 ml PBS, they have been centrifuged with a Beckman centrifuge fitted with a JA 20 rotor at 5000 rpm for 30 min at 4° C. The layer has been treated with 25 ml 6M guanidine HCl in PBS solution and maintained under agitation for 60 min at room temperature. Then the suspensions have been centrifuged, as disclosed above, and the supernatants, 20 ml for each sample, have been dialysed versus PBS for 16 hours at 4° C. After dialysis a further centrifugation is carried out to remove the insoluble material; the obtained supernatants represent the fractions enriched in the protein of about 130 kD associated to the cytoxin.

As shown in FIG. 1 the amount of the protein of about 130 kD obtained from the two cell layers are comparable, however with an excess from the culture obtained by using cyclodextrin from which a larger amount of cell layer has been recovered.

EXAMPLE 2

The liquid cultures of *H. pylori* obtained as reported in Example 1 have been collected by centrifugation and resuspended in 25 ml, 0.25M glycine HCl, 5 mM EDTA, pH 3 and incubated at 37° C. for 16 hours without agitation.

Thus obtained bacteria suspension have been added with 10N NaOH to a pH value of 7.4 and subsequently centrifuged at 12000 rpm for 30 min at 5° C.

Figure 2:
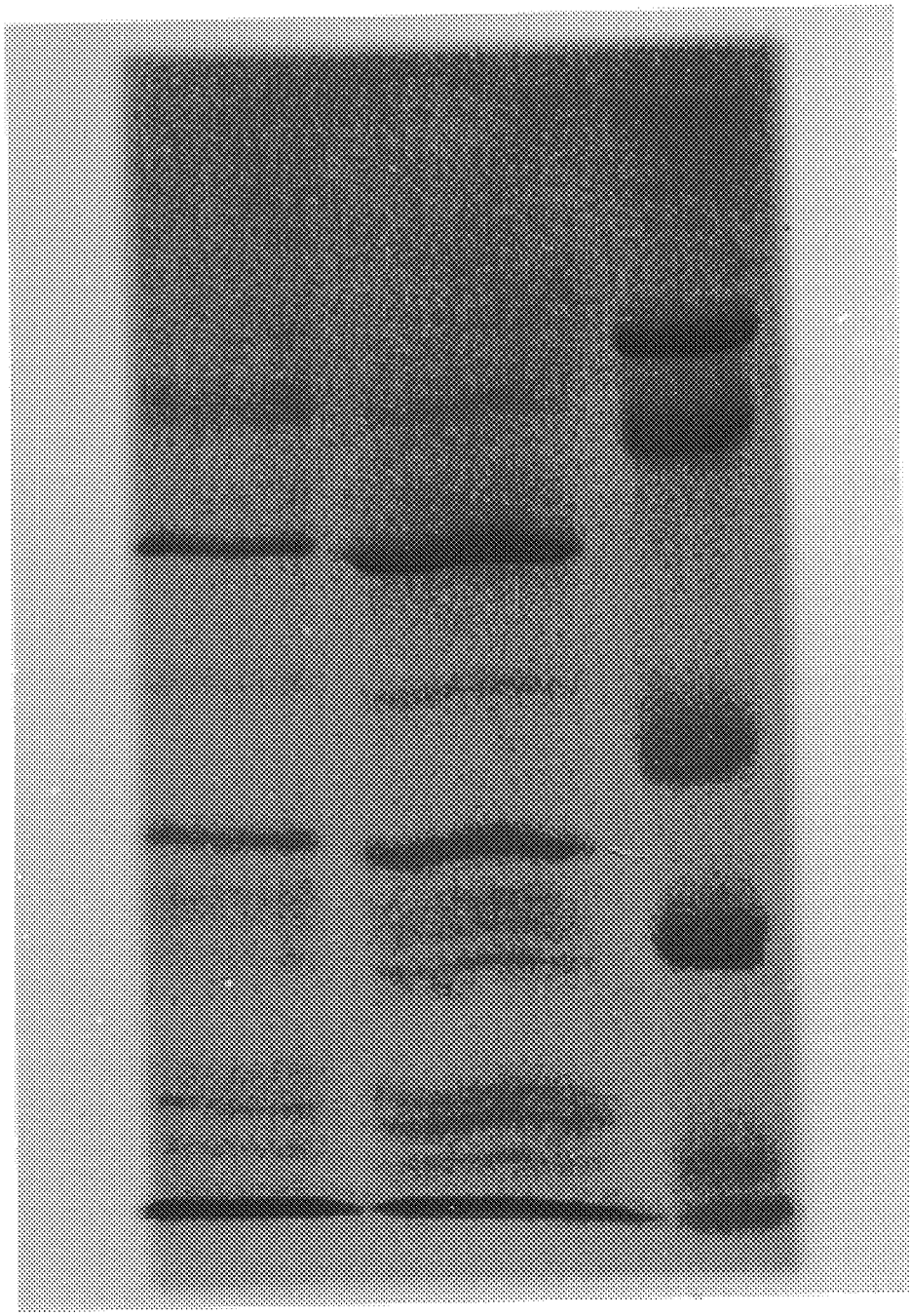
FIG. 2 compares the *H. pylori* cellular layer (urease) obtained in Example 2 with the cellular layer obtained via the traditional media.

Thus obtained supernatants have been quickly cooled in ice/water added with two volumes acetone pre-cooled at −20° C. The suspensions so obtained are maintained at −20° C. for 5 hours and subsequently centrifuged at 12000 rpm. The recovered pellets have been resuspended in 5 ml PBS in order to be dialysed versus PBS at 4° C. for 16 hours. Thus obtained samples represent fractions enriched in urease and they are shown in Fig. 2.

The comparison of the bands puts in evidence that the bands relative to the two major urease subunits i.e. 66 and 29 kD, are nearly equivalent in the two samples.

EXAMPLE 3

Eight strains of *H. pylori*, namely the strain CCUG 17874 and further seven strains isolated from gastric biopsies, have been evaluated for their ability to grow on Columbia agar and on Muller-Hinton agar containing either dimethyl-O-β-cyclodextrin 1 g/l or, in alternative and as comparative term, 50 g/l defibrinated horse blood.

The aforementioned culture media have been further assayed in their selective form obtained upon addition of one of the two chemotherapeutic mixtures reported hereinafter:

Mixture A: 5 mg/l vancomycin, 10 mg/l trimethoprin, 5 mg/l amphotericin B. 5 U/ml polymixin.

Mixture B: As mixture A by replacing polymixin by 6 mg/l cefsulodin.

The strains, maintained in Wilkins-Chalgren media added with 20% glycerol at −80° C., have been thawed, inoculated on dishes of Columbia agar containing 5% defibrinated horse blood and incubated at 37° C. for 72 hours in microaerophylic conditions. Then the bacterial layer from each strain has been suspended in Brucella media up to an optic density of about 6 McFarland. Ten μl of the bacterial suspension have been inoculated on each of the aforementioned dishes and smeared with the technique of the isolation. The dishes have been incubated as reported above and monitored after 5–7 days.

The colonies developed on the media containing cyclodextrin, with or without antibiotics, were about 2 mm in size, were in relief, opaque, regularly cut and with buttery consistence. The features of said colonies did not differ from those of colonies developed on media comprising blood.

The colonies developed on media either with cyclodextrin or with blood showed the same results, peculiar of the species, by the following tests: Gram negative staining; oxidase, catalase and urease positive; nitrate to nitrite reduction; hippurate hydrolysis negative; leucine-aryl-amidase, gamma-glutamyl transpeptidase, acid phosphatase and indoxyl acetate positive.

EXAMPLE 4

Sensitivity assays of *H. pylori* to chemotherapeutics have been carried out using Columbia agar comprising dimethyl-O-β-cyclodextrin. The eight strains reported in example 3 have been examined.

The chemotherapeutics tested according to the Kirby-Bauer method were the following: ampicillin (10 μg flat tablet), erythromycin (15 μg flat tablet), clindamycin (2 μg flat tablet), metronidazole (100 μg tablets), colloidal bismuth subcitrate (De Nol) (100 μg flat tablets).

The metronidazole was also tested according to the method designated E-test (AB Biodisk Solna Sweden).

The tests have been carried out either on Columbia agar comprising 0.1% cyclodextrin or on Columbia agar comprising 5% defibrinated horse blood.

80 ml of the above cited solid culture media were put in Petri dishes of 150 mm.

The strains were suspended in Brucella media up to an optic density of 4 McFarland and subsequently dispensed on the dishes with a sterile cotton wad. After having placed diskettes and strips, the dishes have been maintained for 3–5 days in microaerophylic atmosphere at high level of humidity, at 37° C. After said period of time the inhibition halos of the different chemotherapeutics and the minimum inhibiting concentrations (MIC) of metronidazole have been compared on the dishes containing the media with cyclodextrin and those with defibrinated horse blood. The halos proved to be overlapping.

EXAMPLE 5

Assays of motility on soft agar have been performed using the eight strains disclosed in example 3. The soft agar was prepared by adding, before the sterilisation, 5 g DIFCO agar per litre Brucella media. The compared media were those comprising either 0.1% cyclodextrin or 10% heat inactivated fetal bovine serum.

The inoculation was effected by dipping, about 2 mm, the ring containing the bacterial layer picked up from a dish of agar comprising 0.1% cyclodextrin. Once inoculated, the dishes have been incubated at the same conditions referred to in example 4 and observed after 5 days. Among the eight tested strains, six showed diffusion within the depth of the agar of both media, which indicates motility, whereas the remaining two did not evidence any diffusion in both media.

EXAMPLE 6

Specimens from 10 patients subjected to diagnostic gastroscopy for dyspepsy have been examined. From each patient 5 biopsy specimens have been collected from the stomach cavity: one for the histological test; one for the culture on Columbia agar comprising 0.1% dimethyl-O-β-cyclodextrin, 5 mg/l vancomycin, 10 mg/l trimethoprim, 6 mg/l cefsulodin, 5000U/1 polymixin and 5 mg/l amphotericin B; one for the culture on Columbia agar comprising 5% defibrinated blood plus the chemoterapeutic mixture cited above; one for the bacterioscopic examination upon staining of the smears of biopsies on slide with acridine orange; one for the determination of the urease activity.

The dishes have been incubated in microaerophylia at 37° C. and examined after 48 hours and daily during 7 days.

The suspected colonies were identified as *H. pylori* by following the procedure disclosed in example 3.

*H. pylori* was isolated in 5 cases: in three cases on both media, in one case on cyclodextrin media only and in a further case on blood media only. The *H. pylori* colonies on Columbia agar with cyclodextrin were already well visible after 48 hours; by the fifth day the colony sizes were similar to those developed on Columbia agar comprising blood. The selectivity of the two media in relation to the bacteria accompanying *H. pylori* in the same specimen from the biopsy proved to be identical. This experimentation confirms the suitability of cyclodextrin comprising media for the primary isolation of *H. pylori* from gastric biopsies.

In FIG. 1 and 2 there are reported the results obtained from the electrophoresis of the cellular layer obtained in example 1 and 2 respectively (lane CD in each figure) compared with the cellular layer obtained with the traditional media (lanes SF). Lane C in both figures indicates the standards for the determination of the molecular weight. The electrophoresis was performed in 7% SDS-PAGE on mini-gel according to the method of Laemmli U.K., employing an electrophoretic cell Mini-Protean 2 Biorad$^R$ at 200 V for 45 min. The protein bands were stained with Coomassie$^R$ R-250.

The invention claimed is:

1. A method for the culture of microorganisms of the genera Helicobacter, Campylobacter, and Arcobacter, comprising culturing said microorganisms in a culture medium useful for cultivating said microorganisms containing blood products and/or derivatives thereof, wherein the blood products and/or derivatives thereof are replaced by a β-cyclodextrin, optionally methylated.

2. A method for culturing a primary isolate of *Helicobacter pylori* comprising
   a) harvesting a specimen from the stomach cavity of a patient exhibiting symptoms of dyspepsia; and
   b) culturing said specimen in a culture medium useful for cultivating the microorganism containing blood products and/or derivatives thereof, wherein blood products and/or derivatives thereof are replaced by a β-cyclodextrin, optionally methylated.

\* \* \* \* \*

UNITED STATES PATENT AND TRADEMARK OFFICE
CERTIFICATE OF CORRECTION

| | |
|---|---|
| PATENT NO. | : 5,900,372 |
| DATED | : May 4, 1999 |
| INVENTOR(S) | : Figura et al. |

It is certified that error appears in the above-identified patent and that said Letters Patent is hereby corrected as shown below:

Item [56] References Cited:
Please insert "FOREIGN PATENT DOCUMENTS" before "OTHER PUBLICATIONS".
Please insert "0 296 765 A2, 12/1988, European Patent Off." after "FOREIGN PATENT DOCUMENTS".

Signed and Sealed this

Eleventh Day of September, 2001

Attest:

Nicholas P. Godici

Attesting Officer

NICHOLAS P. GODICI
*Acting Director of the United States Patent and Trademark Office*